(12) United States Patent
Chen et al.

(10) Patent No.: US 10,633,325 B1
(45) Date of Patent: Apr. 28, 2020

(54) O-PHENYL PHENOXYALKYL ACRYLATE AND METHODS FOR PRODUCING THE SAME

(71) Applicant: China Petrochemical Development Corporation, Taipei (Taiwan), Kaohsiung (TW)

(72) Inventors: Yu-Sen Chen, Kaohsiung (TW); Min-Chia Huang, Kaohsiung (TW); Yu-Chiao Liu, Kaohsiung (TW); Chih-Wei Chang, Kaohsiung (TW)

(73) Assignee: China Petrochemical Development Corporation, Taipei (Taiwan), Kaohsiung (TW)

( * ) Notice: Subject to any disclaimer, the term of this patent is extended or adjusted under 35 U.S.C. 154(b) by 0 days.

(21) Appl. No.: 16/446,957

(22) Filed: Jun. 20, 2019

(30) Foreign Application Priority Data

Oct. 24, 2018 (TW) .............................. 107137544 A

(51) Int. Cl.
| | | |
|---|---|---|
| *C07C 67/02* | (2006.01) | |
| *B01J 31/02* | (2006.01) | |
| *B01J 31/38* | (2006.01) | |
| *C08K 5/57* | (2006.01) | |

(52) U.S. Cl.
CPC ........... *C07C 67/02* (2013.01); *B01J 31/0212* (2013.01); *B01J 31/38* (2013.01); *C08K 5/57* (2013.01); *B01J 31/0211* (2013.01); *B01J 2231/49* (2013.01); *B01J 2531/002* (2013.01)

(58) Field of Classification Search
CPC ...... C07C 67/02; C07C 69/03; B01J 31/0212; B01J 31/0211; B01J 31/38; B01J 2231/49; B01J 2431/002; C08K 5/57; C07F 7/003
See application file for complete search history.

(56) References Cited

U.S. PATENT DOCUMENTS 6,130,270 A * 10/2000 Ukon ....................... G02B 1/04
522/182

FOREIGN PATENT DOCUMENTS

CN 103709033 A * 4/2014 ............ C07C 67/08

OTHER PUBLICATIONS

Liu, C., et al., Synthesis of biphenyl methacrylate (BPMA) monomer, American Chemical Society: Division of Polymer Chemistry, National Meeting 224th Boston MA. 1 page (Year: 2002).*
Hyun, S-H, et al., Synthesis and characterization of polymers with moiety of 2-phenoyphenol as a mocrobicide, Polyme (Korea), 27( 5), pp. 443-446, CAS abstract 4 pages (Year: 2003).*
Yu Mingdong, et al., CN 203709033 (A), o-phenyl phenoxyethyl acrylate preparation method, English translation, 8 pages (Year: 2014).*

* cited by examiner

*Primary Examiner* — Yate' K Cutliff
(74) *Attorney, Agent, or Firm* — Mintz Levin Cohn Ferris Glovsky and Popeo, P.C.; Peter F. Corless; Steven M. Jensen

(57) ABSTRACT

The present disclosure provides a method for preparing o-phenyl phenoxyalkyl acrylate, including: transesterifying an acrylate-based compound with a biphenyl alcohol compound in the absence of a solvent and in the presence of a catalyst and a polymerization inhibitor to prepare the o-phenyl phenoxyalkyl acrylate represented by the following formula (II),

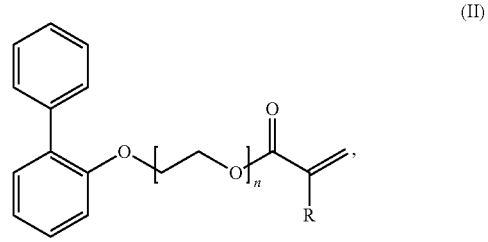

(II)

wherein the catalyst is a compound containing a tin element or a titanium element. According to the method of the present disclosure, the o-phenyl phenoxyalkyl acrylate having transparency and high refractive index can be obtained. Moreover, the method of the present disclosure has the characteristics of high conversion rate and high selectivity, and does not need to add other organic solvents, so that many purification processes can be saved, and the production cost is effectively reduced, which has the value of industrial application.

18 Claims, No Drawings

O-PHENYL PHENOXYALKYL ACRYLATE AND METHODS FOR PRODUCING THE SAME

REFERENCE TO RELATED APPLICATION

This application claims foreign priority under 35 U.S.C. § 119(a) to Patent Application No. 107137544, filed on Oct. 24, 2018, in the Intellectual Property Office of Ministry of Economic Affairs, Republic of China (Taiwan, R.O.C.), the entire content of which Patent Application is incorporated herein by reference.

TECHNICAL FIELD

The present disclosure relates to a method for preparing o-phenyl phenoxyalkyl acrylate, and more particularly to a method for preparing an o-phenyl phenoxyalkyl acrylate without an additional solvent.

BACKGROUND OF THE INVENTION

Acrylates containing aromatic rings are mainly used in optical materials such as optical films, optical lenses, optical lenses and optical resins owing to their good transparency and high refractive index. Among them, o-phenyl phenoxyalkyl acrylate is most suitable for high gloss and high transparency in these fields. Recently, the o-phenyl phenoxyalkyl acrylate has been widely used in, for example, wear-resistant optic materials, scratch-resistant, wear-resistant and self-repairing brightening film coatings, high refractive index brightening coatings, and optical lens.

The traditional method for preparing the o-phenyl phenoxyalkyl acrylate is esterification synthesis. Although the preparation method has the characteristics of high yield, the preparation method requires an organic solvent, so that the solvent needs to be separated through the purification process. Since the purification process needs to be performed at a high temperature, it is difficult to avoid the occurrence of polymerization, even if a polymerization inhibitor is used. Also, the reaction conditions are severe, the reaction time is long, and the process is cumbersome.

In view of the above, it is necessary to propose a method for preparing o-phenyl phenoxyalkyl acrylate without adding additional organic solvents to solve the problems of the prior art.

SUMMARY OF THE INVENTION

In order to solve the above problems, the present disclosure provides a method for preparing an o-phenyl phenoxyalkyl acrylate, comprising: transesterifying an acrylate-based compound with a biphenyl alcohol compound represented by following formula (I),

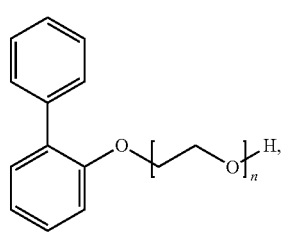

(I)

in the presence of a catalyst and a polymerization inhibitor and in the absence of a solvent to prepare the o-phenyl phenoxyalkyl acrylate represented by following formula (II),

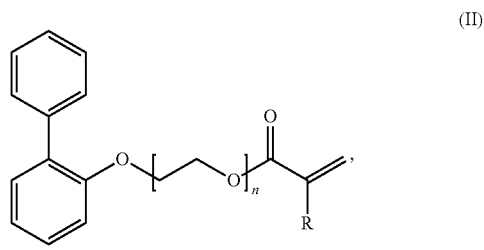

(II)

wherein R represents hydrogen or methyl, and n represents an integer from 0 to 8, and wherein the catalyst is a homogeneous catalyst selected from the group consisting of a tin compound and a titanium compound, and wherein the tin compound is free of a carboxyl group and halogen.

In the method for preparing the o-phenyl phenoxyalkyl acrylate of the present disclosure, the acrylate-based compound is used as a reaction solvent, and a combination of a specific catalyst and a polymerization inhibitor is used to prepare the O-phenyl phenoxyalkyl acrylate of good transparency and high refractive index. The o-phenyl phenoxyalkyl acrylate has the characteristics of high conversion rate and high selectivity, and the preparation method of the present disclosure does not need to add other organic solvent in the reaction process, thereby having the value of industrial application owing to the effective reduction for production cost of the post-treatment and the harm to the environment.

DETAILED DESCRIPTION OF THE INVENTION

The following embodiments of the present disclosure are described by way of specific examples, and those skilled in the art can readily understand the advantages and functions of the present disclosure. The present disclosure may be embodied or applied in various other embodiments. The various details of the present disclosure may be variously modified and changed without departing from the spirit and scope of the present disclosure. In addition, all ranges and values herein are inclusive and combinable. Any value or point falling within the scope recited herein, such as any integer, may be the minimum or maximum value to derive the lower range and the like.

According to the present disclosure, a method for preparing an o-phenyl phenoxyalkyl acrylate comprises: transesterifying an acrylate-based compound with a phenyl alcohol compound of the following formula (I), in the presence of a catalyst and a polymerization inhibitor and in the absence of a solvent,

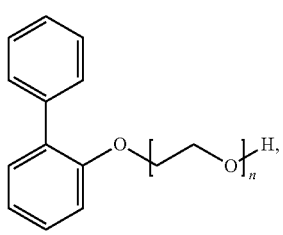

(I)

to prepare an o-phenyl phenoxyalkyl acrylate of the following formula (II)

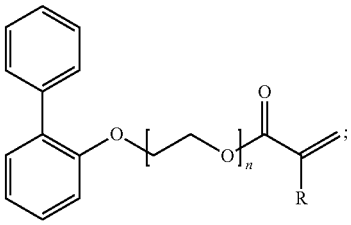

(II)

wherein the catalyst is a homogeneous catalyst selected from a group consisting of a tin compound and titanium compound, and wherein the tin compound is free of carboxyl group and halogen; and n represents an integer from 0 to 8, and R represents hydrogen or methyl.

In an aspect of an embodiment, the acrylate-based compound is represented by a structure of the formula (III):

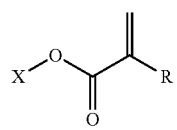

(III)

wherein R represents hydrogen or methyl; and X represents C1-C4 alkyl, and particularly preferably C1-C2 alkyl.

In an aspect of an embodiment, the acrylate-based compound is one selected from a group consisting of methyl acrylate, ethyl acrylate, methyl methacrylate and ethyl methacrylate.

In an aspect of an embodiment, the biphenyl alcohol compound of the formula (I) is preferably 2-(2-biphenyloxy) ethanol.

Regarding the biphenyl alcohol compound of the formula (I), parameter conditions for reaction temperature of transesterification reaction, compositions of azeotrope, and distillation temperature thereof, catalyst amounts and reaction time, owing to the large steric hindrance of the biphenyl group in the molecular structure thereof, are different from those of the general acrylate and linear alkyl alcohol.

First, in the preparation method of the present disclosure, the catalyst may be a homogeneous catalyst or a heterogeneous catalyst, and particularly preferably a homogeneous catalyst.

The tin compound catalyst includes an organotin salt or a tin compound having a structure of the formula (IV);

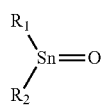

(IV)

wherein $R_1$ and $R_2$ are C1-C10 alkyl or hydrogen; and $R_1$ and $R_2$ of the tin compound catalyst having the structure of the formula (IV) are the same or different, and respectively represent alkyl of carbon numbers 1, 2, 3, 4, 5, 6, 7, 8, 9 to 10.

In an aspect of an embodiment, the tin compound catalyst is a homogeneous catalyst and is at least one individually selected from a group consisting of dioctyltin oxide and dibutyltin oxide, or is selected from a group consisting of monobutyltin oxide, dibutyltin maleate and stannous octoate.

In an aspect of an embodiment, the tin compound catalyst is a homogeneous catalyst such as bis-(C1-C10)alkyl tin oxide. Preferably, the bis-(C1-C10)alkyl tin oxide is at least one selected from a group consisting of dioctyl tin oxide and dibutyl tin oxide, and the recommended amount of the bis-(C1-C10)alkyl tin oxide is from 0.5 to 1.5% by weight.

The titanium compound catalyst is a titanate catalyst, wherein the titanate catalyst is a homogeneous catalyst represented by the formula (V):

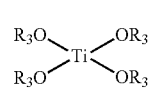

(V)

wherein $R_3$ is C1-C4 alkyl, and C1-C4 alkyl may be a linear or branched alkyl.

Preferably, the titanate is tetrabutyl titanate or tetraisopropyl titanate. In another embodiment, the recommended amount of the titanate catalyst is from 1.5 to 3.5% by weight.

By using the above tin compound or titanium compound as the catalyst of the present disclosure, the selectivity and conversion rate of o-phenyl phenoxyalkyl acrylate can be effectively improved, and side reactions can be reduced, and compared with the reaction process using compounds of Group IA metal and Group IIA metal, the o-phenyl phenoxyalkyl acrylate produced has higher gloss and high transparency. On the other hand, in a specific aspect of an embodiment, when a tin compound is used as a catalyst, a tin compound having a carboxyl group or a halogen can be excluded to maintain a high conversion rate. Further, the tin compound catalyst is preferably oxidized bis-(C1-C10)alkyl tin oxide to improve the conversion rate as compared with monoalkyltin oxide. Moreover, when two kinds of compounds are used as the catalyst, the compound having the Group IA metal and the Group IIA metal is also avoided as much as possible.

The purpose of the polymerization inhibitor is to prevent polymerization of the acrylate-based compound, wherein the polymerization inhibitor is at least one selected from a group consisting of oxygen, phenothiazine, a phenolic compound, and a nitroxide free-radical compound.

The oxygen polymerization inhibitor is present in the form of steam, so that not only the polymerization of the acrylate-based compound of the reaction solution but also the polymerization of the acrylate-based compound condensed on the upper portion of the reactor can be effectively prevented. In an aspect of the embodiment, the oxygen polymerization inhibitor is oxygen, and is supplied by air, and is preferably dry air.

In an aspect of an embodiment, the nitroxide free-radical compound is a piperidinyl nitroxide free-radical compound or a piperidine nitroxide phosphite, or a complex of the two, such as 2,2,6,6-tetramethylpiperidine-1-oxyl radical or tris-(2,2,6,6-tetramethylpiperidine nitroxide) phosphite.

In an aspect of an embodiment, the phenolic compound is 6-tert-butyl-2,4-dimethylphenol, 2-tert-butyl hydroquinone, 2,5-di-tert-butyl hydroquinone, p-hydroxyanisole or hydroquinone.

According to the present disclosure, the polymerization inhibitor is present in an amount of from 0.1 to 1.5% by weight. In an aspect of an embodiment, the polymerization inhibitor is the phenolic compound, and the recommended amount of the phenolic compound is from 0.5 to 1.5% by weight.

The method for preparing the o-phenyl phenoxyalkyl acrylate of the present disclosure is a transesterification reaction using an acrylate-based compound and a biphenyl alcohol compound, and the reaction equation is as follows:

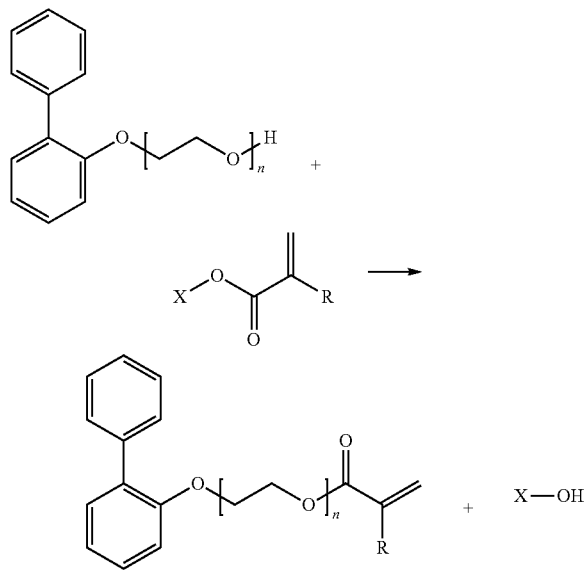

wherein n, X and R are as defined in the foregoing disclosure.

The method for preparing the o-phenyl phenoxyalkyl acrylate of the present disclosure is a method for preparing o-phenyl phenoxyalkyl acrylate without adding additional organic solvents to the reaction system thereof, and is characterized in that an amount of the acrylate-based compound exceeds an amount for the reaction, so that the acrylate-based compound is used as a reaction solvent, and there is no need for additional organic solvent. As such, the operation is simple, the reaction cost is low, the environment is less likely to be contaminated, and the polymerization phenomenon caused by the solvent is reduced as well.

In an aspect of an embodiment, a molar ratio of the acrylate-based compound to the biphenyl alcohol compound is from 2.5:1 to 4:1, wherein the molar ratio of the acrylate-based compound to the biphenyl alcohol compound to be 2.5:1 to 3.5:1 is particularly preferred. If the molar ratio of the acrylate-based compound to the biphenyl alcohol compound is less than 2.5:1, the transesterification reaction is to be slowed; if the molar ratio of the acrylate-based compound to the biphenyl alcohol compound is higher than 4:1, there would cause problems of deteriorated productivity and complicated post-reaction processing.

According to a preferred embodiment of the present disclosure, the preparation method uses a batch reactor with a reactive distillation apparatus. Further, in the transesterification reaction, an azeotrope containing the acrylate-based compound and the by-product of alcohol is distilled off using a distillation apparatus. By this method, an azeotrope having a specific composition ratio of the by-product of alcohol and the acrylate-based compound formed during the reaction is to be distilled out of the reaction system, and based on the Le Chatelier principle, the transesterification reaction can be continued.

According to the present disclosure, the specific preparation method comprises that after feeding a catalyst, a polymerization inhibitor, a acrylate-based compound and a biphenyl alcohol compound, a temperature is raised to the reaction temperature; the reaction is first carried out under total reflux conditions for a period of time, and then the reflux ratio is adjusted to maintain the distillation column overhead temperature in a range of 60 to 80° C.; and the azeotrope composed of the by-product of alcohol and the acrylate-based compound is removed by azeotropic distillation.

In order to control the amount of distillate of azeotrope to avoid affecting the conversion rate and selectivity of the transesterification reaction, the distillation apparatus is preferably used with a number of plates of 5 to 10, and the transesterification reaction temperature is controlled to be in a range of 110 to 120° C. The transesterification reaction temperature is better not higher than 120° C. to avoid side reactions such as coloring and polymerization.

In an aspect of an embodiment, the reflux ratio of the distillation apparatus is preferably from 1.2 to 2.

In an aspect of an embodiment, the transesterification reaction time is 4 to 6 hours.

In an aspect of an embodiment, the transesterification reaction is usually carried out under normal pressure and in an atmosphere of air or an inert gas, wherein the inert gas system includes a gas such as nitrogen, argon or helium.

In an aspect of an embodiment, the transesterification reaction takes place under continuous stirring.

The method for preparing the o-phenyl phenoxyalkyl acrylate of the present disclosure further includes that after the transesterification reaction, the unreacted acrylate-based compound is separated by reduced pressure distillation.

In an aspect of an embodiment, the o-phenyl phenoxyalkyl acrylate product after reduced pressure distillation can be further filtered to more purify the product.

The o-phenyl phenoxyalkyl acrylate obtained by the above preparation method of the present disclosure has good transparency and high refractive index, and is advantageously used in products such as optical materials.

The present disclosure is further described in detail by way of examples.

Example 1

Ethyl acrylate (1800 g, 17.98 mole), 2-(2-biphenyloxy) ethanol (OPPEO) (1100 g, 5.13 mole), 1% by weight of polymerization inhibitor, 6-tert-butyl-2,4-dimethylphenol and 1.4% by weight of dioctyltin oxide were placed as catalysts in a round bottom flask, and the mixture was heated to about 110 to 120° C. At the same time, the overhead temperature of the upper distillation apparatus was controlled at 78° C. to allow the ethyl acrylate and the by-product of ethanol to form an azeotrope to be distilled off, and the reactant in the flask was subjected to a transesterification reaction for about 4 hours; after the reaction is completed, the unreacted acrylate-based compound was separated by reduced pressure distillation; and finally, the o-phenyl phenoxyalkyl acrylate product after reduced pressure distillation treatment was subjected to filtration and purification to obtain an o-phenyl phenoxyalkyl acrylate product having the conversion rate of 92% and the selectivity of more than 97%.

According to the standard test method of ASTM-D1209, the o-phenyl phenoxyalkyl acrylate product was taken as 100 ml of sample liquid, using a chromatic aberration meter (HunterLab Color Quest XE) and a platinum-cobalt standard solution (Apha chromaticity values were respectively 5, 10, 15, 30, 50, 100, and 500) for colorimetric analysis. The o-phenyl phenoxyalkyl acrylate product was found to have an Apha color value of 24.

Example 2

The preparation method was the same as Example 1, except that the dioctyltin oxide was replaced by 3% by weight of tetraisopropyl titanate, and the transesterification reaction time was 6 hours. Thus, an o-phenyl phenoxyalkyl acrylate product having an Apha color value of more than 500 can be obtained with the conversion rate of 90% and the selectivity of greater than 95%.

Example 3

The preparation method was the same as Example 1, except that the dioctyltin oxide was replaced with 1.4% by weight of dibutyltin oxide, and the transesterification reaction time was 4 hours. An o-phenyl phenoxyalkyl acrylate product having an Apha color value greater than 500 was obtained with the conversion rate of 88% and the selectivity of greater than 97%.

Example 4

The preparation method is the same as Example 1, except that the dioctyltin oxide was replaced by 3% by weight of tetrabutyl titanate, and the transesterification reaction time is 6 hours. Thus, an o-phenyl phenoxyalkyl acrylate product having an APHA color value of more than 500 was obtained with the conversion rate of 71% and the selectivity of greater than 95%.

Comparative Example 1

The preparation method was the same as Example 1, except that the dioctyltin oxide was replaced with 1% by weight of potassium titanate, and the transesterification reaction time was 6 hours. The conversion rate thereof was 24%, and the selectivity was more than 97%.

Comparative Example 2

The preparation method was the same as Example 1, except that the dioctyltin oxide was replaced with 3% by weight of calcium oxide, and the transesterification reaction time was 4 hours. The conversion rate thereof was 8%, and the selectivity was more than 97%.

Comparative Example 3

The preparation method was the same as Example 1, except that the dioctyltin oxide was replaced with 1% by weight of calcium carbonate, and the transesterification reaction time was 2 hours. There was no conversion effect.

Comparative Example 4

The preparation method was the same as Example 1, except that the dioctyltin oxide was replaced with 0.1% by weight of lithium chloride, and the transesterification reaction time was 4 hours. There was no conversion effect.

Comparative Example 5

Methyl acrylate (388 g, 4.51 mole), 2-(2-biphenyl)ethanol (642.78 g, 3.00 mole), 0.13% by weight of p-hydroxyanisole (MEHQ), 0.05% by weight of hydroquinone as a polymerization inhibitor, 0.4% by weight of dimethyltin dichloride and 0.11% by weight of sodium methoxide as a catalyst were placed in a round bottom flask, and the mixture was heated. At the same time, the temperature of the overhead of the distillation apparatus is maintained at 58° C., so that the methyl acrylate and by-product of methanol were formed as azeotrope to be distilled off, and the reactant in the flask was subjected to a transesterification reaction. The reaction time was about 6 hours, and there was no conversion effect.

Given the forgoing, the o-phenyl phenoxyalkyl acrylate of the present disclosure is prepared by using an acrylate-based compound as a reaction solvent, and a combination of a specific catalyst and a polymerization inhibitor are used to prepare the o-phenyl phenoxyalkyl acrylate having the good transparency and high refractive index with characteristics of high conversion rate and high selectivity. Also, the preparation method of the present disclosure does not need to add other organic solvent in the reaction process, so as to have the value of industrial application owing to the effective reduction for production cost of the post-treatment and the harm to the environment.

The above embodiments are merely illustrative and not intended to limit the present disclosure. Modifications and variations of the above examples can be made by those skilled in the art without departing from the spirit and scope of the present disclosure. Therefore, the scope of the present disclosure is defined by the scope of the claims of the present disclosure, and the scope of the present disclosure is not to be construed as being limited thereto.

What is claimed is:

1. A method for preparing o-phenyl phenoxyalkyl acrylate, comprising:
transesterifying an acrylate-based compound with a biphenyl alcohol compound represented by following formula (I),

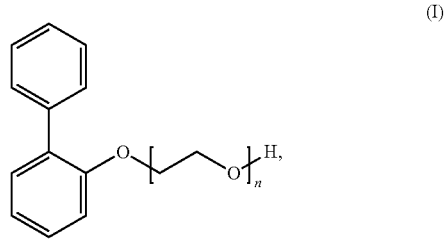

in the absence of a solvent and in the presence of a catalyst and a polymerization inhibitor to prepare the o-phenyl phenoxyalkyl acrylate represented by following formula (II),

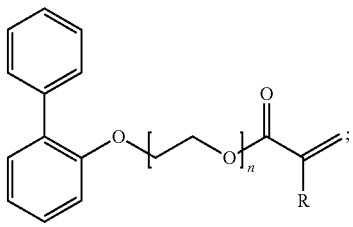
(II)

wherein R represents hydrogen or methyl, and n represents an integer of from 0 to 8, and wherein the catalyst is a homogeneous catalyst selected from the group consisting of a tin compound and a titanium compound, and wherein the tin compound is free of halogen and a carboxyl group.

2. The method of claim 1, wherein the homogeneous catalyst is bis-(C1-C10)alkyl tin oxide.

3. The method of claim 2, wherein the bis-(C1-C10)alkyl tin oxide is at least one selected from the group consisting of dioctyltin oxide and dibutyltin oxide.

4. The method of claim 2, wherein the bis-(C1-C10)alkyl tin oxide is in an amount of from 0.5% to 1.5% by weight.

5. The method of claim 1, wherein the homogeneous catalyst is a titanate catalyst.

6. The method of claim 5, wherein the titanate catalyst is at least one selected from the group consisting of tetrabutyl titanate and tetraisopropyl titanate.

7. The method of claim 5, wherein the titanate catalyst is in an amount of from 1.5% to 3.5% by weight.

8. The method of claim 1, wherein the polymerization inhibitor is at least one selected from the group consisting of oxygen, phenothiazine, a phenolic compound, and a nitroxide free-radical compound.

9. The method of claim 8, wherein the phenolic compound is 6-tert-butyl-2,4-dimethylphenol, 2-tert-butyl hydroquinone, 2,5-di-tert-butyl hydroquinone, p-hydroxyanisole or hydroquinone.

10. The method of claim 8, wherein the nitroxide free-radical compound is piperidinol nitroxide or piperidine nitroxide phosphite.

11. The method of claim 1, wherein the polymerization inhibitor is in an amount of from 0.1% to 1.5% by weight.

12. The method of claim 8, wherein the polymerization inhibitor is the phenolic compound in an amount of from 0.5% to 1.5% by weight.

13. The method of claim 1, wherein the acrylate-based compound is selected from the group consisting of methyl acrylate, ethyl acrylate, methyl methacrylate and ethyl methacrylate.

14. The method of claim 1, wherein the transesterification is performed with a molar ratio of the acrylate-based compound to the biphenyl alcohol compound represented by the formula (I) from 2.5:1 to 4:1.

15. The method of claim 1, wherein the transesterification is performed in a reaction temperature from 110° C. to 120° C.

16. The method of claim 15, wherein the transesterification is performed in a reaction time from 4 hours to 6 hours.

17. The method of claim 1, further comprising distilling off an azeotrope containing the acrylate-based compound and a byproduct of alcohol by using a distillation apparatus in the transesterification.

18. The method of claim 1, further comprising separating an unreacted acrylate-based compound by reduced pressure distillation after the transesterification.

* * * * *